(12) United States Patent
Ni et al.

(10) Patent No.: US 8,966,954 B2
(45) Date of Patent: Mar. 3, 2015

(54) ANTHROPOMORPHIC PHANTOM FOR MEDICAL IMAGING SYSTEMS

(75) Inventors: Yu-Ching Ni, Taoyuan County (TW);
Shiang-Lin Hsu, Taoyuan County (TW);
Meei-Ling Jan, Taoyuan County (TW)

(73) Assignee: Institute of Nuclear Energy Research Atomic Energy Council, Executive Yuan, Taoyuan County (TW)

( * ) Notice: Subject to any disclaimer, the term of this patent is extended or adjusted under 35 U.S.C. 154(b) by 452 days.

(21) Appl. No.: 13/412,847

(22) Filed: Mar. 6, 2012

(65) Prior Publication Data

US 2013/0104678 A1 May 2, 2013

(30) Foreign Application Priority Data

Oct. 31, 2011 (TW) .............................. 100139589 A (51) Int. Cl.
*G01N 29/30* (2006.01)
*G09B 23/30* (2006.01)
*G09B 23/28* (2006.01)

(52) U.S. Cl.
CPC .............. *G09B 23/30* (2013.01); *G09B 23/286* (2013.01)
USPC .......................................................... 73/1.86

(58) Field of Classification Search
None
See application file for complete search history.

(56) References Cited

U.S. PATENT DOCUMENTS

| 7,059,168 B2 * | 6/2006 | Hibi et al. ...................... 73/1.86 |
| 2004/0067591 A1 * | 4/2004 | Madsen et al. .................... 436/8 |
| 2013/0108999 A1 * | 5/2013 | Gillies et al. .................. 434/272 |
| 2013/0157240 A1 * | 6/2013 | Hart et al. ..................... 434/267 |

* cited by examiner

*Primary Examiner* — Robert R Raevis
(74) *Attorney, Agent, or Firm* — WPAT, PC; Justin King (57) ABSTRACT

An anthropomorphic phantom for medical imaging systems is disclosed, which is configured with organ models designed to mimic the three-dimensional shape of human organs, and also by the arrangement of plate-like first connecting elements inside their corresponding organ models, lesion phantoms for simulating tumors can be fixedly secured inside the corresponding organ model using a plurality of first connection holes formed on the first connecting element. Therefore, by the distribution of those first connection holes, not only the lesion phantoms can be arranged at any position inside the corresponding organ model at will as required, but also by modularized design of the anthropomorphic phantom, organ models can first be assembled to form a module structure while the whole module structure with the organ model can be moved into and assembled easily with a torso-like humanoid housing of the anthropomorphic phantom by the use of a handle element.

9 Claims, 9 Drawing Sheets

ANTHROPOMORPHIC PHANTOM FOR MEDICAL IMAGING SYSTEMS

FIELD OF THE INVENTION

The present invention relates to a medical imaging technique, and more particularly, to an anthropomorphic phantom for medical imaging systems.

BACKGROUND OF THE INVENTION

Figure 6:
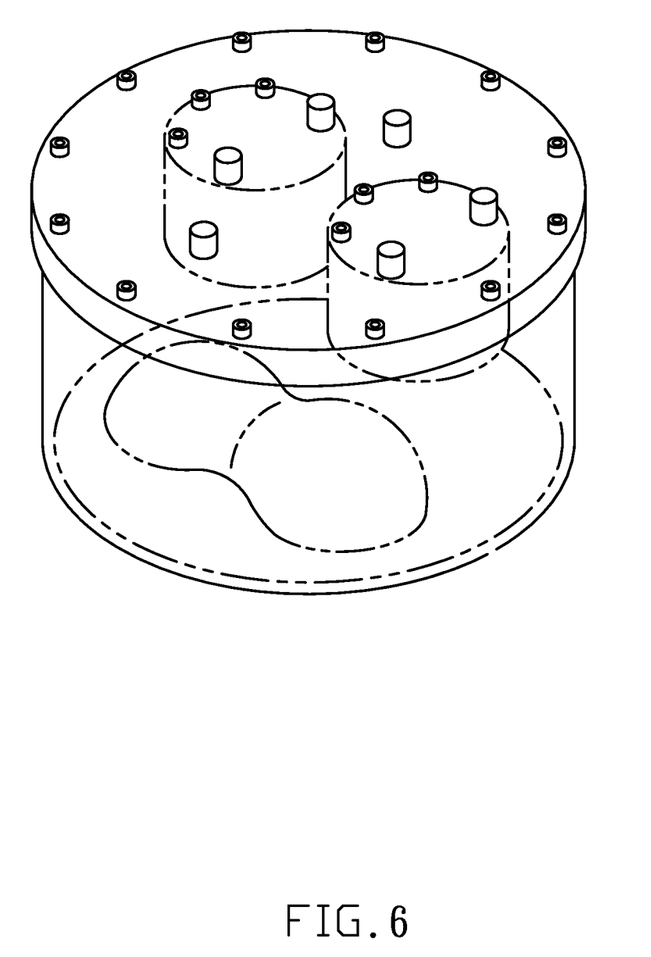
FIG. 6 is a schematic diagram showing a prior-art anthropomorphic torso phantom by Data Spectrum Corporation.

Notably, there are already many anthropomorphic phantoms available on the market. One of which is an anthropomorphic torso phantom by Data Spectrum Corporation, as shown in FIG. 6. In FIG. 6, although the anthropomorphic torso phantom is configured with a heart, a breast, a portion of lung, a liver and a spinal cord, only the heart, breast, liver and torso can be filled by a solution of contrast agent or medicine. Moreover, it is disadvantage in that except for a specific position on the breast, there is no space available in all the other organs that can be used for allowing any spherical tumor/lesion phantom to be arranged thereat. Thus, the aforesaid prior-art anthropomorphic torso phantom is not useful in medical imaging researches for tumors and lesions.

Figure 7:
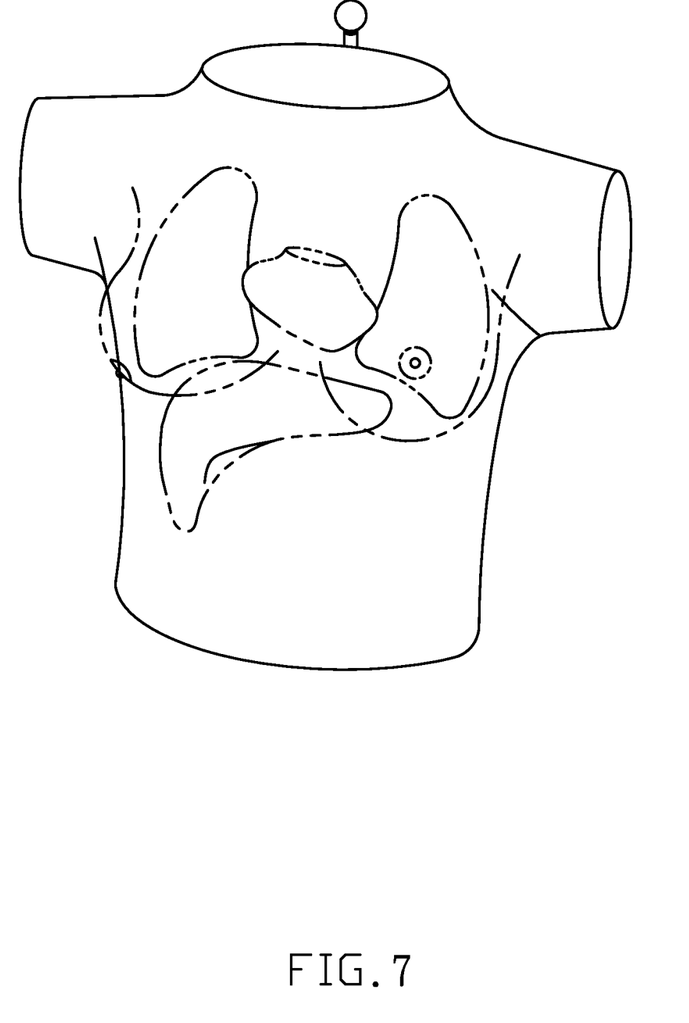
FIG. 7 is a schematic diagram showing a prior-art thorax phantom by Fluke Biomedical Corporation.

Another such anthropomorphic phantom is the thorax phantom by Fluke Biomedical Corporation that is also configured with a heart, a lung, a liver and a breast, as shown in FIG. 7. Although it is designed for allowing all the organs including the heart, lung, liver and breast to be filled by solutions of contrast agent or medicine, only the heart and the breast are formed with specific spaces to be used for receiving spherical tumor/lesion phantoms while all the other organs are not configured with such space. Thus, the aforesaid prior-art thorax phantom is also not useful in medical imaging researches for tumors and lesions.

Figure 8:
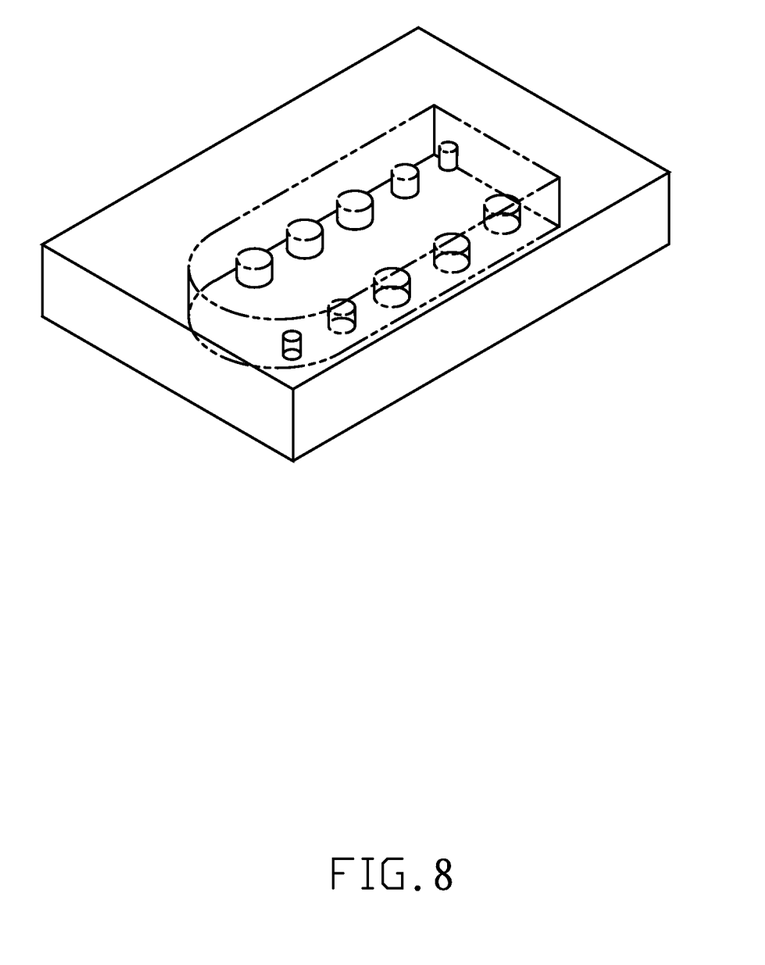
FIG. 8 is a schematic diagram showing a prior-art Williams liver phantom by Bright Technologies Corporation.

On the other hand, different from the aforesaid humanoid phantoms, there are some other phantoms on the market that each is designed to simulate a specific internal organ, such as liver. One such phantom is the Williams liver phantom by Bright Technologies Corporation, as shown in FIG. 8. In FIG. 8, the Williams liver phantom is configured with five hollow cylinders and five solid cylinders, whereas the hollow cylinders are used for allowing solutions of contrast agents or medicines to fill therein and the solid cylinders are used for simulating lesions. It is noted that the smallest cylinder is about 3 mm in diameter. In addition to the sizes as well as the positions of those cylinders are fixed and can not be changed, the appearance of the cylinder too simple to mimic a real lesion.

Figure 9:
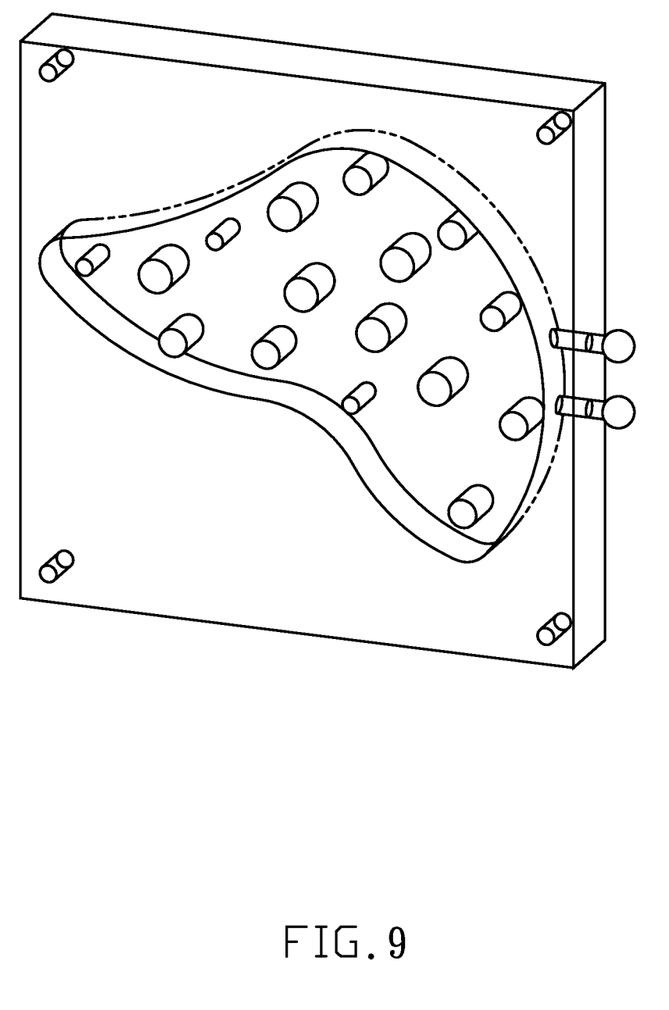
FIG. 9 is a schematic diagram showing a prior-art multi-contrast/resolution phantom by Fluke Biomedical Corporation.

Moreover, another internal organ phantom is the multicontrast/resolution phantom by Fluke Biomedical Corporation, as shown in FIG. 9. The multicontrast/resolution phantom, being a liver-shaped hollow phantom that are designed to be filled by solutions of contrast agents or medicines, is configured with a plurality of acrylic lesion phantoms of different sizes. Although the aforesaid prior-art multicontrast/resolution phantom can be used for generating lesion images of different contrasts and resolutions, it is still not a complete 3D liver and also is disadvantageous in that the sizes as well as the positions of those acrylic lesion phantoms are fixed and can not be changed.

In addition, for the phantoms disclosed in FIG. 6 and FIG. 7, they are not formed with any space to be used for allowing any spherical tumor/lesion phantom to be arranged thereat. Not to mention that the phantom of FIG. 6 is not shaped like a complete liver.

Therefore, it is in need of an anthropomorphic phantom for medical imaging systems capable of overcoming the aforesaid shortcomings

SUMMARY OF THE INVENTION

The object of the present invention is to provide an anthropomorphic phantom for medical imaging systems, that is configured with organ models that are designed to mimic the three-dimensional shape of human organs while allowing solutions of contrast agents or medicines to be filled therein, and also by the arrangement of a plate-like first connecting element inside each of the corresponding organ models, lesion phantoms that are used for simulating tumors are fixedly secured inside the corresponding organ model by the use of a plurality of first connection holes that are arranged distributing on the first connecting element. Moreover, by the distribution of those first connection holes, not only each of the lesion phantoms can be arranged at any position inside the corresponding organ model at will as required, but also there can be more than one lesion phantoms either of the same size or of different sizes to be arranged inside the same organ model simultaneously. Thereby, the anthropomorphic phantom can very adaptive for simulating real lesions in human body.

Another object of the invention to provide an anthropomorphic phantom with modularized design, by that an organ model can first be fixedly secured to a second connecting element of a module structure while the whole module structure with the organ model can be assembled into a torso-like humanoid housing of the anthropomorphic phantom by the use of a handle element. Thereby, not only the assembling of organ model to the torso-like humanoid housing can be simplified, but also any experimental error causing by contamination of contrast agents or medicines can be prevented.

To achieve the above objects, the present invention provides an anthropomorphic phantom for medical imaging systems, comprising: a hollow humanoid housing; at least one hollow organ model, removably disposed inside the humanoid housing, and each being composed of a top portion and a bottom portion in a manner that the top portion is detachably connected to the bottom portion; and at least one first connecting element, each being a plate-like structure that is configured with at least one first connection hole while being removably arranged inside one corresponding organ model at a position between the top portion and bottom portion.

In an embodiment of the invention, the top portion and the bottom portion is detachably connected to each other by the use of a plurality of bolts.

In another embodiment of the invention, the anthropomorphic phantom further comprises: at least one second connecting element, each being a plate-like structure that is removable arranged inside the humanoid housing while being configured with at least one organ connection hole and at least one second connection hole for allowing one corresponding organ model to be removably secured to the organ connection hole.

In another embodiment of the invention, the anthropomorphic phantom further comprises: at least one lesion phantom, each being removably secured to the corresponding first connection hole or the corresponding second connection hole.

In another embodiment of the invention, the anthropomorphic phantom comprises: a plurality of said second connecting elements, being arranged for allowing any two neighboring second connecting elements to couple with each other while allowing a space to be formed therebetween; and a plurality of said organ models; wherein, the amount of the second connecting elements is not larger than that of the plural organ models.

In another embodiment of the invention, each second connecting element is connected to a handle element, which is extendedly disposed on the outside of the humanoid housing.

In another embodiment of the invention, the handle element is composed of a handle, a cap and a plurality of connection rods in a manner that the handle is disposed outside the cap while the cap is disposed covering the humanoid housing, and each connection rod is disposed for allowing an end thereof to connect to a side of the cap that is facing away from handle and another end to be removably fixed to one second connection hole of its corresponding second connecting element by the use of a bolt.

In another embodiment of the invention, the anthropomorphic phantom comprises: a plurality of said second connecting elements, being arranged for allowing any two neighboring second connecting elements to couple with each other by the use of the connection rods that each is removably connected respectively to the two neighboring second connecting elements by the two ends thereof, while allowing a space to be formed therebetween; and a plurality of said organ models; wherein, the amount of the plural organ model is equal to that of the second connecting elements.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as the follows.

Figure 1:
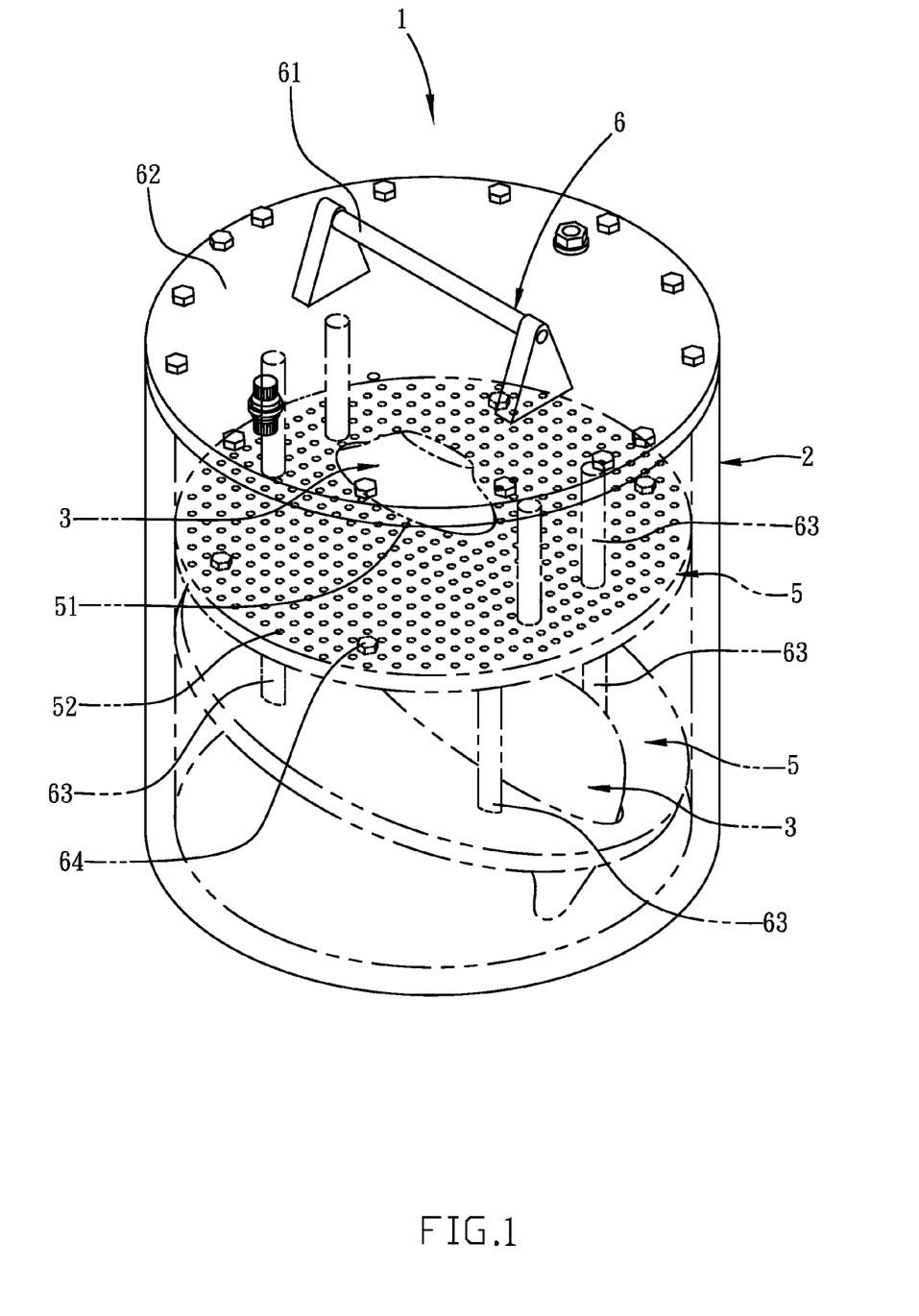
FIG. 1 is a perspective diagram showing an anthropomorphic phantom with cylinder-shape housing according to an embodiment of the present invention.
Figure 2:
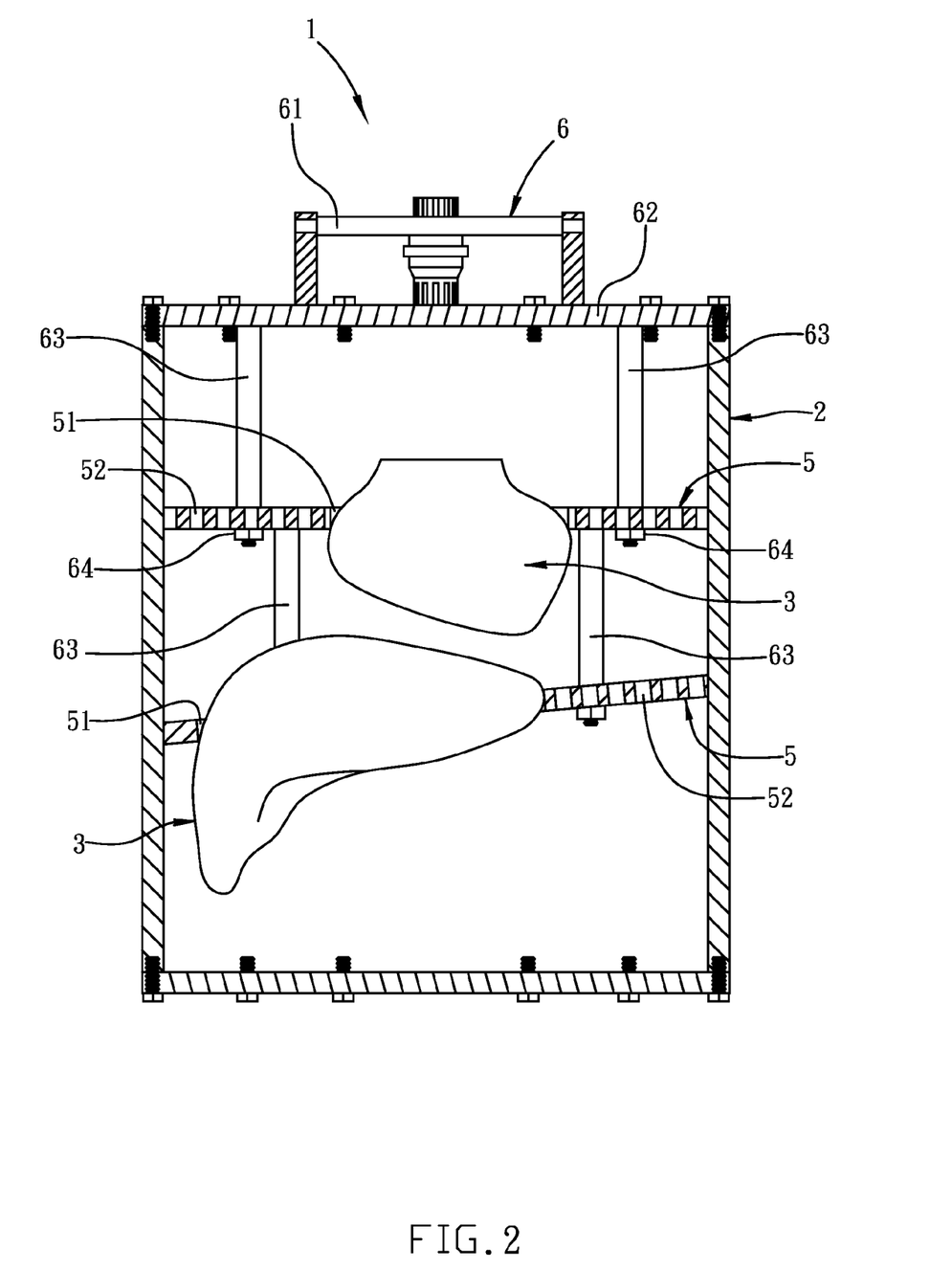
FIG. 2 is a cross sectional view of FIG. 1.
Figure 3:
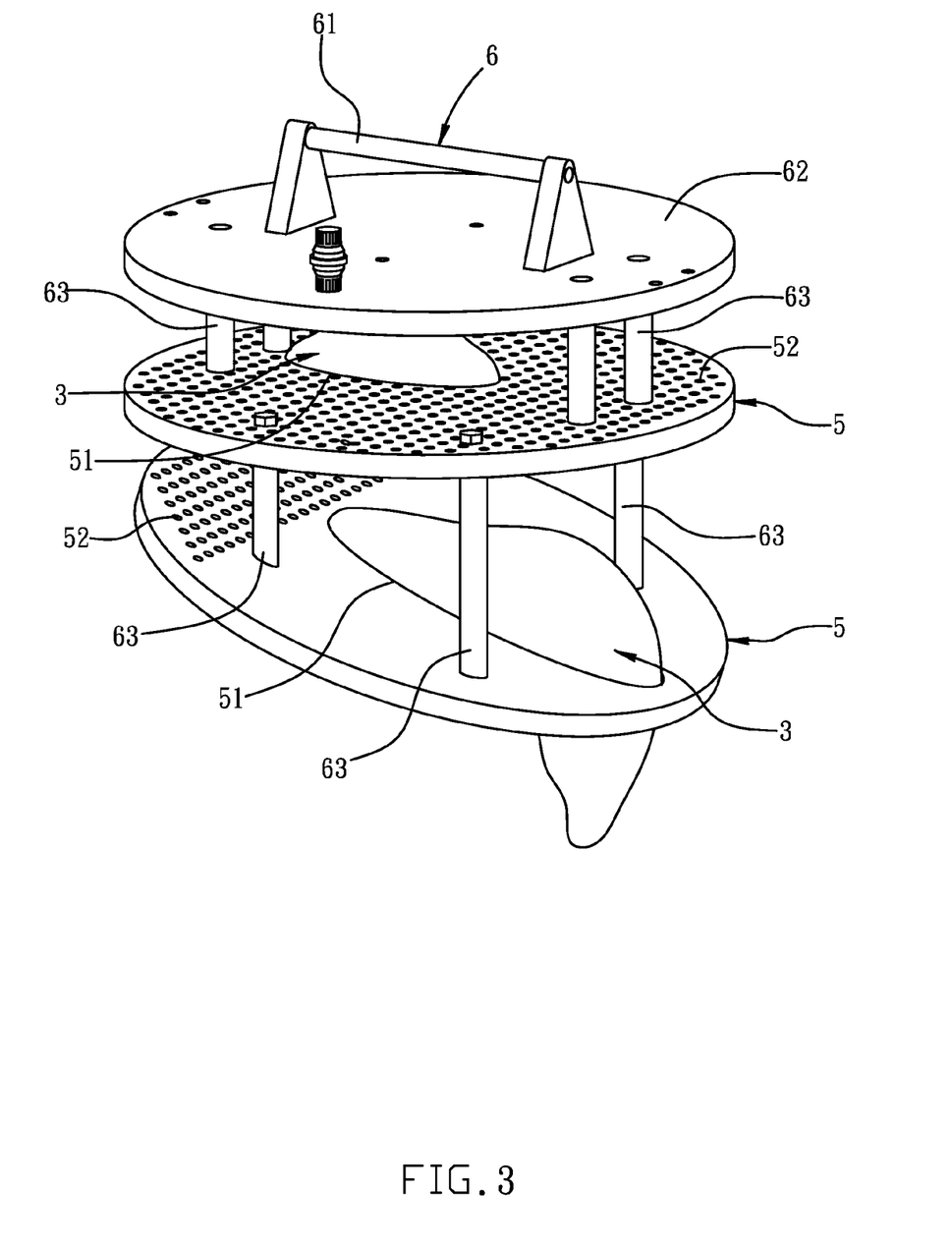
FIG. 3 is a three-dimensional diagram showing the structure inside the humanoid housing of an anthropomorphic phantom according to an embodiment of the present invention.
Figure 4:
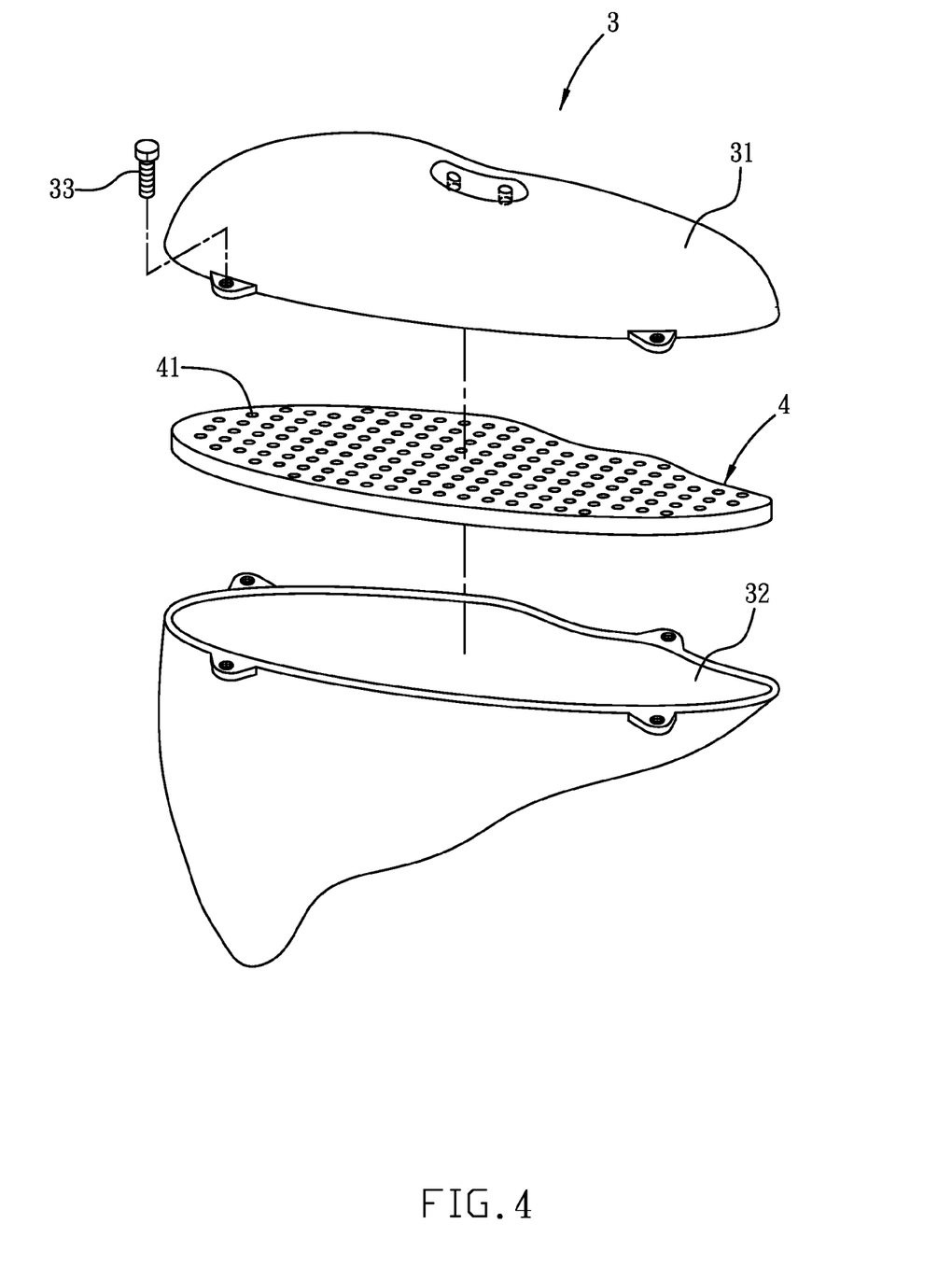
FIG. 4 is a schematic diagram showing a liver-shape organ model that is adapted for an anthropomorphic phantom of the present invention.
Figure 5:
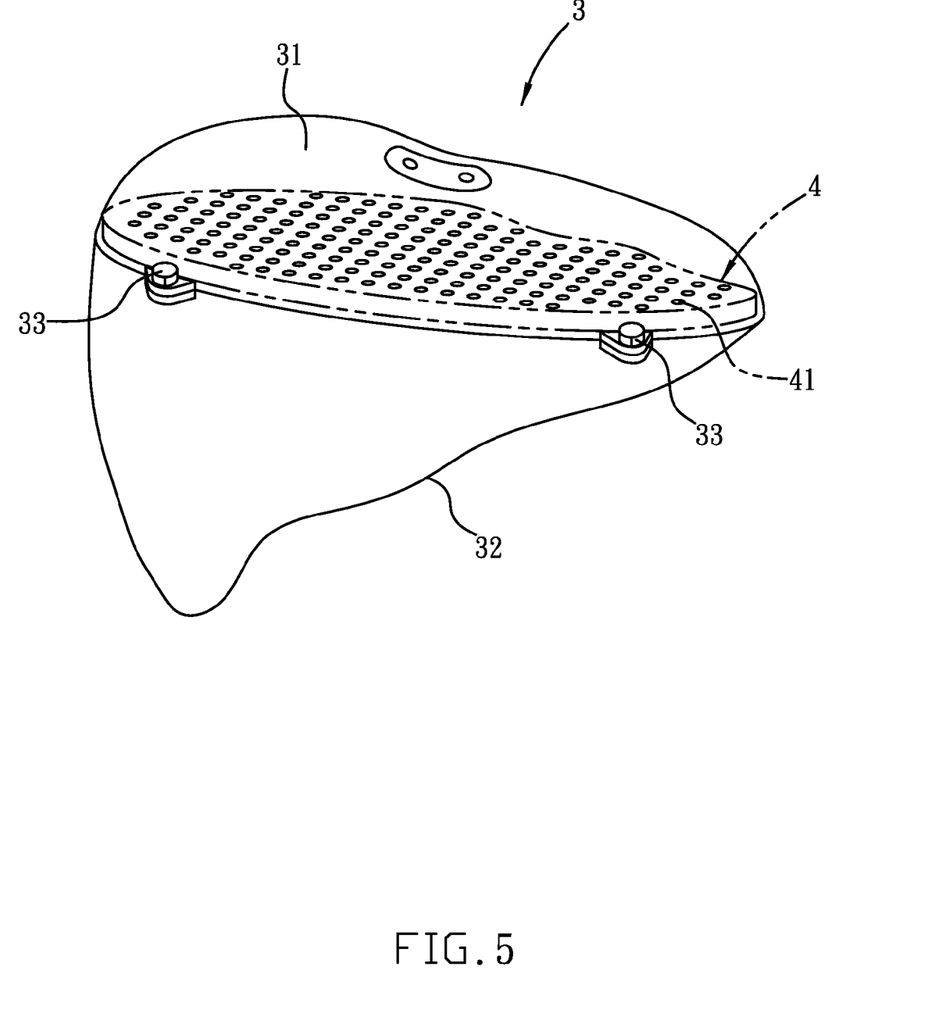
FIG. 5 is a perspective view of a liver-shape organ model that is adapted for an anthropomorphic phantom of the present invention.

FIG. 1 is a perspective diagram showing an anthropomorphic phantom with cylinder-shape housing according to an embodiment of the present invention. FIG. 2 is a cross sectional view of FIG. 1. FIG. 3 is a three-dimensional diagram showing the structure inside the humanoid housing of an anthropomorphic phantom according to an embodiment of the present invention. FIG. 4 is a schematic diagram showing a liver-shape organ model that is adapted for an anthropomorphic phantom of the present invention. FIG. 5 is a perspective view of a liver-shape organ model that is adapted for an anthropomorphic phantom of the present invention.

The anthropomorphic phantom 1 of the present invention comprises: a humanoid housing 2, at least one organ model 3, and a first connecting element 4. In an embodiment of the invention, the humanoid housing 2, being a hollow structure, is formed as a cylinder. Nevertheless, the humanoid housing 2 can be formed as a human torso.

Moreover, each organ model 3 is a hollow structure that is removably disposed inside the humanoid housing 2. In the embodiment shown in FIG. 1, there are two organ models, i.e. a heart and a liver. In addition, for the embodiments shown in FIG. 4 and FIG. 5, the liver-shaped organ model is used for illustration. As shown in FIG. 4 and FIG. 5, the organ model 3 is composed of a top portion 31 and a bottom portion 32 in a manner that the top portion 31 is detachably connected to the bottom portion 32. Preferably, the top portion 31 is detachably connected to the bottom portion 32 by the use of a plurality of bolts 33.

Moreover, the first connecting element 4 is formed as a plate-like structure that is configured with at least one first connection hole 41 while being removably arranged inside one corresponding organ model 3 at a position between the top portion 31 and bottom portion 32 thereof. It is noted that by the arrangement of the first connection hole 41, there can be a plurality of lesion phantoms to be removably arranged inside the organ model 3.

With the design of the organ model 3 and the first connecting element 4, a three-dimensional human organ, such as the liver, can be mimicked while allowing solutions of contrast agents or medicines to be filled therein, and also by the arrangement of the plate-like first connecting element 4 inside the liver-shaped organ model, spherical lesion phantoms that are used for simulating tumors can be fixedly secured inside the corresponding organ model by the use of a plurality of first connection holes 41 that are arranged distributing on the first connecting element 4. Moreover, by the distribution of those first connection holes 41, not only each of the lesion phantoms can be arranged at any position inside the corresponding organ model at will as required, but also there can be more than one lesion phantoms either of the same size or of different sizes to be arranged inside the same organ model simultaneously. Thereby, the anthropomorphic phantom can very adaptive for simulating real lesions in human body.

In an embodiment of the invention, the anthropomorphic phantom further comprises: at least one second connecting element 5, each being a plate-like structure that is removable arranged inside the humanoid housing 2 while being configured with at least one organ connection hole 51 and at least one second connection hole 52 for allowing one corresponding organ model 3 to be removably secured to the organ connection hole 51, and also allowing a plurality of lesion phantoms to be removably secured to their corresponding second connection holes 52. It is noted that the amount of the plural organ models 3 can be equal to or, in some case, larger than that of the second connecting elements 5. In addition, any two neighboring second connecting elements 5 should be arranged coupling with each other while allowing a space to be formed therebetween; and by the formations of those spaces between neighboring second connecting elements 5, a plurality of said organ models 3 of various sizes can be received therebetween.

In an embodiment of the invention, each second connecting element 5 is connected to a handle element 6, which is extendedly disposed on the outside of the humanoid housing 2; and the handle element 6 is composed of a handle 61, a cap 62 and a plurality of connection rods 63 in a manner that the handle 61 is disposed outside the cap 62 while the cap 62 is disposed covering the humanoid housing 2, and each connection rod 63 is disposed for allowing an end thereof to connect to a side of the cap 62 that is facing away from handle 61 and another end to be removably fixed to one selected second connection hole 52 of its corresponding second connecting element 5 by the use of a bolt 64. When there are more than two second connecting elements, as shown in FIG. 1, FIG. 2 and FIG. 3, any two neighboring second connecting elements 5 is coupled with each other by the use of the connection rods 63 that each is removably connected respectively to the two neighboring second connecting elements 5 by the two ends thereof. Thereby, a modularized design is achieved so as to ease the assembling and disassembling.

Operationally, by the modularized structure achieved in the anthropomorphic phantom, the organ models 3 are first being fixed to their corresponding second connecting elements 5 so as to form a plurality of independent modules, and then each of the plural modules can be moved and assembled into a torso-like humanoid housing 2 of the anthropomorphic phantom by the use of the handle element 6, without having to secure each of the organ models into a torso-like humanoid housing 2 in a one-by-one manner, or even in a specific order. Thereby, not only the assembling of organ model to the torso-like humanoid housing can be simplified, but also any experimental error causing by contamination of contrast agents or medicines can be prevented.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

What is claimed is:

1. An anthropomorphic phantom for medical imaging systems, comprising:
    a hollow humanoid housing;
    at least one organ model, removably disposed inside the humanoid housing, and each being composed of a top portion and a bottom portion in a manner that the top portion is detachably connected to the bottom portion; and
    at least one first connecting element, each being in substance a plate-like structure that is configured with at least one first connection hole while being removably arranged inside one corresponding organ model at a position between the top portion and bottom portion thereof.

2. The anthropomorphic phantom of claim 1, wherein the at least one organ model is a hollow structure.

3. The anthropomorphic phantom of claim 1, wherein the top portion and the bottom portion of the same organ model is detachably connected to each other by the use of a plurality of bolts.

4. The anthropomorphic phantom of claim 1, further comprising:
    at least one second connecting element, each being in substance a plate-like structure that is removable arranged inside the humanoid housing while being configured with at least one organ connection hole and at least one second connection hole for allowing one corresponding organ model to be removably secured to the organ connection hole.

5. The anthropomorphic phantom of claim 4, further comprising:
    at least one lesion phantom, each being removably secured to the corresponding second connection hole.

6. The anthropomorphic phantom of claim 4, wherein each second connecting element is connected to a handle element, which is extendedly disposed on the outside of the humanoid housing.

7. The anthropomorphic phantom of claim 6, wherein the handle element is composed of a handle, a cap, and a plurality of connection rods, wherein the handle is disposed above the cap while the cap is disposed covering the humanoid housing, and each connection rod is disposed for allowing an end thereof to connect to a side of the cap that is facing away from handle and another end to be removably fixed to one selected second connection hole of its corresponding second connecting element by the use of a bolt.

8. The anthropomorphic phantom of claim 7, further comprises:
    a plurality of said second connecting elements;
    a plurality of connection rods, connecting two neighboring second connecting elements; and
    a plurality of said organ models;
    wherein, the amount of the second connecting elements is equal to or smaller than that of the plural organ models.

9. The anthropomorphic phantom of claim 1, further comprising:
    at least one lesion phantom, each being removably secured to the corresponding first connection hole.

* * * * *